(12) United States Patent
Russell et al.

(10) Patent No.: US 11,992,295 B2
(45) Date of Patent: May 28, 2024

(54) BLOOD SENSOR ASSEMBLY

(71) Applicant: Merit Medical Systems, Inc., South Jordan, UT (US)

(72) Inventors: Rick Russell, Cottonwood Heights, UT (US); Scott Brown, Riverton, UT (US); Jonathan Cheney, West Jordan, UT (US); Luca Salmaso, Ango (CH)

(73) Assignee: Merit Medical Systems, Inc., South Jordan, UT (US)

( * ) Notice: Subject to any disclaimer, the term of this patent is extended or adjusted under 35 U.S.C. 154(b) by 258 days.

(21) Appl. No.: 17/209,663

(22) Filed: Mar. 23, 2021

(65) Prior Publication Data

US 2021/0298613 A1 Sep. 30, 2021

Related U.S. Application Data

(60) Provisional application No. 63/082,227, filed on Sep. 23, 2020, provisional application No. 62/993,824, filed on Mar. 24, 2020.

(51) Int. Cl.
| | | |
|---|---|---|
| *A61B 5/0205* | (2006.01) | |
| *A61B 5/00* | (2006.01) | |
| *A61B 5/021* | (2006.01) | |
| *A61M 1/36* | (2006.01) | |

(52) U.S. Cl.
CPC ...... *A61B 5/02055* (2013.01); *A61B 5/02141* (2013.01); *A61B 5/6866* (2013.01); *A61M 1/3609* (2014.02); *A61M 1/3623* (2022.05); *A61M 1/3639* (2013.01); *A61M 1/3666* (2013.01); *A61M 1/369* (2013.01); *A61B 2562/0247* (2013.01); *A61B 2562/0271* (2013.01); *A61B 2562/166* (2013.01); *A61M 2230/30* (2013.01); *A61M 2230/50* (2013.01)

(58) Field of Classification Search
None
See application file for complete search history.

(56) References Cited

U.S. PATENT DOCUMENTS

| | | | |
|---|---|---|---|
| 5,871,627 | A | 2/1999 | Abraham-Fuchs et al. |
| 7,021,148 | B2 | 4/2006 | Kuhn et al. |
| 2004/0050168 | A1 | 3/2004 | Uberreiter |
| 2009/0057789 | A1 | 3/2009 | Huang et al. |
| 2010/0030137 | A1 | 2/2010 | Hall et al. |
| 2011/0009800 | A1 | 1/2011 | Dam et al. |

(Continued)

FOREIGN PATENT DOCUMENTS

| | | |
|---|---|---|
| JP | 06028660 | 2/2006 |
| WO | 2018154407 | 8/2018 |

OTHER PUBLICATIONS

International Search Report and Written Opinion dated Jan. 5, 2023 for PCT/US2022/076814.

(Continued)

*Primary Examiner* — Jay B Shah
(74) *Attorney, Agent, or Firm* — Dorsey & Whitney LLP

(57) ABSTRACT

Devices used to sense physiologic blood parameters are disclosed. The devices may be configured to sense at least two physiologic blood parameters at substantially a common site of an extracorporeal perfusion circuit. The devices may include a pressure sensor and a temperature sensor. The temperature sensor may be in direct contact with the blood.

16 Claims, 10 Drawing Sheets

(56) References Cited

U.S. PATENT DOCUMENTS

| | | |
|---|---|---|
| 2012/0042734 A1 | 2/2012 | Wade et al. |
| 2012/0095351 A1 | 4/2012 | Klose et al. |
| 2015/0247774 A1 | 9/2015 | Wagner et al. |
| 2015/0292954 A1 | 10/2015 | Takeda |
| 2017/0115169 A1* | 4/2017 | Busche ................. G01K 11/00 |
| 2017/0326282 A1* | 11/2017 | Wilt .................... A61M 1/1639 |
| 2018/0110913 A1 | 4/2018 | Loderer et al. |
| 2020/0061278 A1* | 2/2020 | Vargas Fonseca ... A61B 5/6866 |

OTHER PUBLICATIONS

International Search Report and Written Opinion dated Jul. 6, 2021 for PCT/US2021/023690.
Extended European Search Report dated Mar. 5, 2024 for EP21775452.2.

* cited by examiner

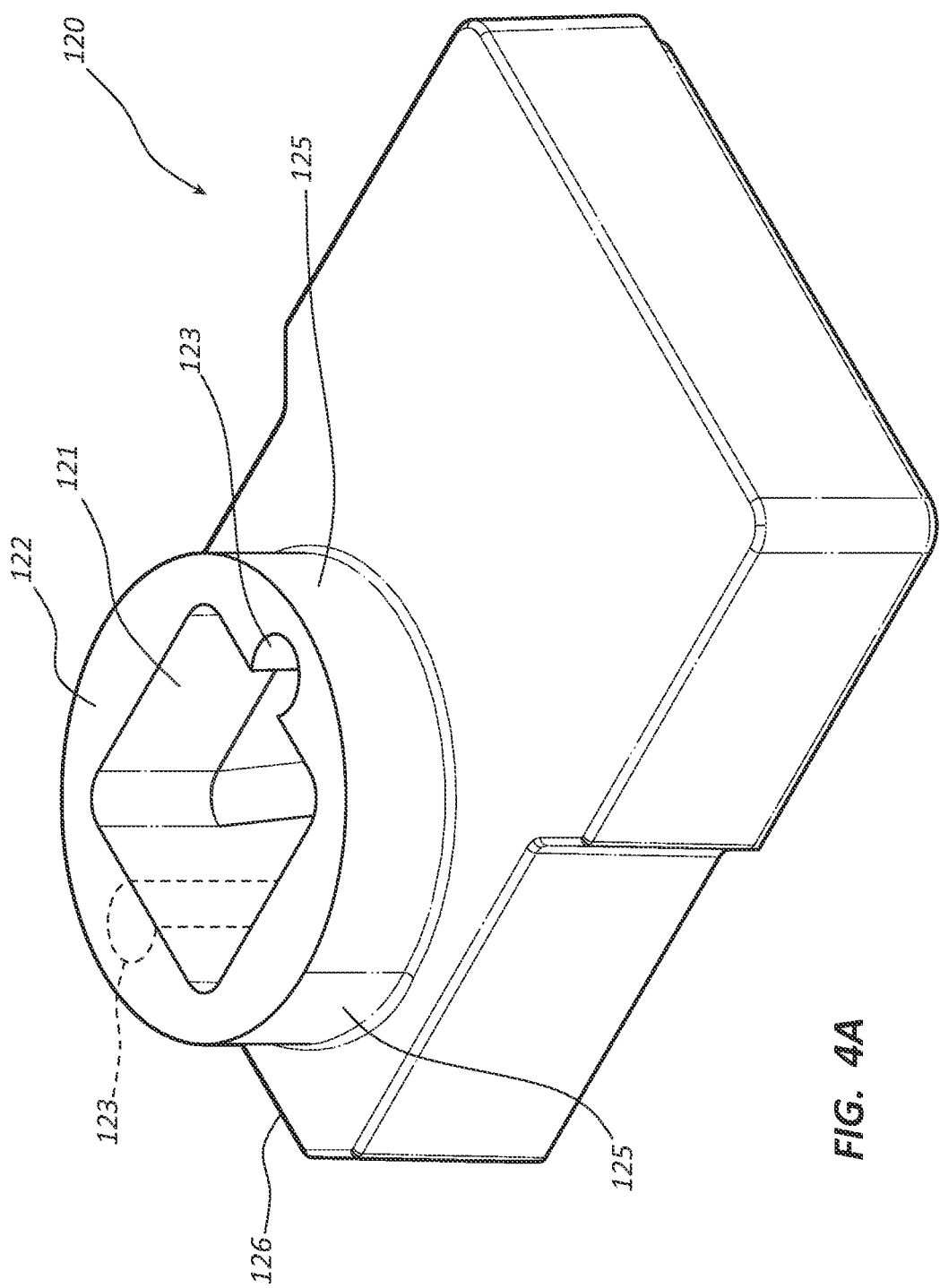

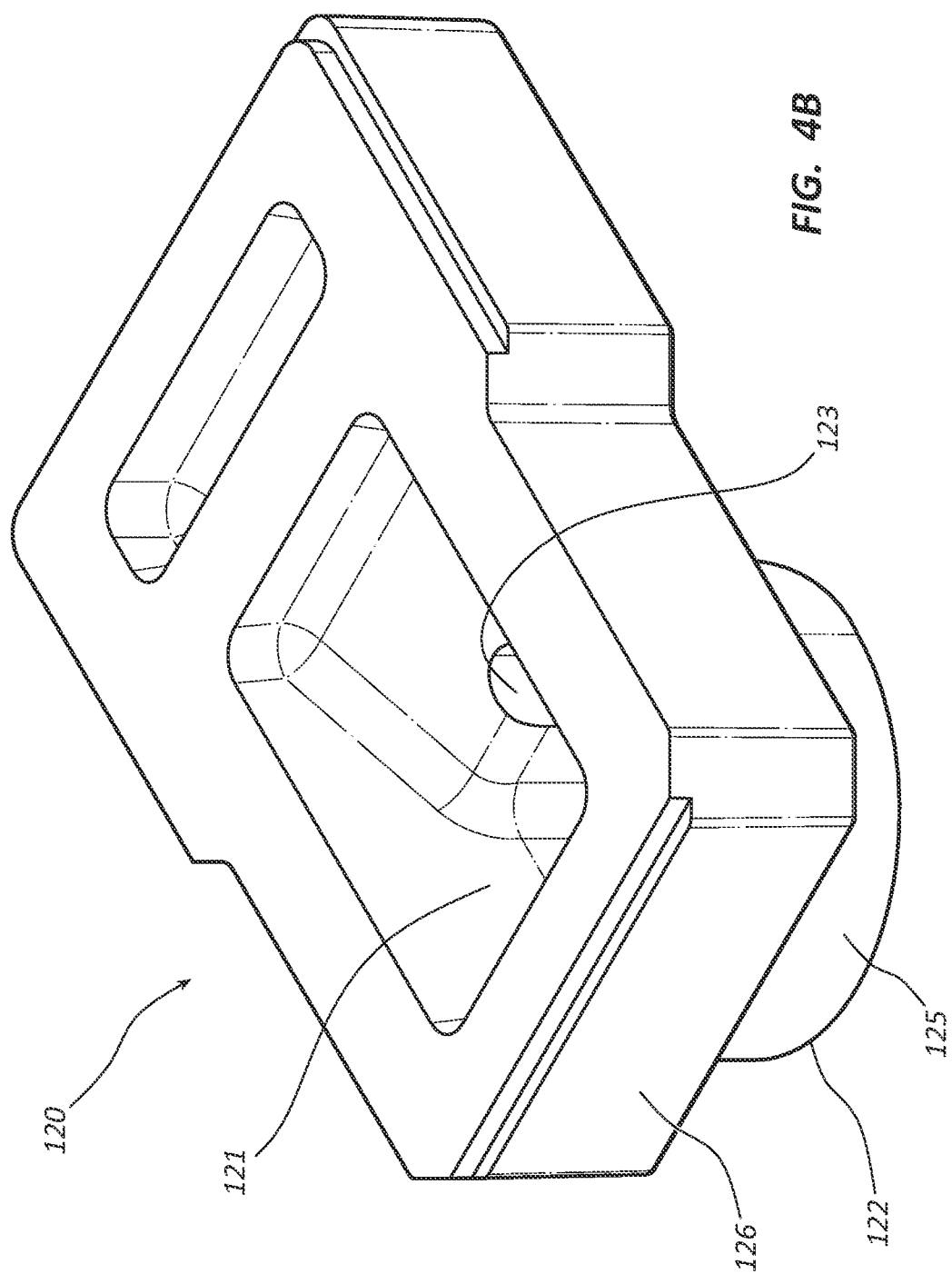

BLOOD SENSOR ASSEMBLY

RELATED APPLICATIONS

This application claims priority to U.S. Provisional Application No. 62/993,824, filed on Mar. 24, 2020 and titled, "Blood Sensor Assembly," and U.S. Provisional Application No. 63/082,227, filed on Sep. 23, 2020 and titled, "Blood Sensor Assembly," both of which are hereby incorporated by reference in their entireties.

TECHNICAL FIELD

The present disclosure relates generally to devices used to sense physiologic parameters of blood. In some embodiments, the present disclosure relates to sensing devices used to measure blood pressure and blood temperature at a common point of measurement or location.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 4A is a top perspective view of a gel well housing of the sensor device of FIG. 2.

FIG. 4B is a bottom perspective view of the gel well housing of the sensor device of FIG. 2.

DETAILED DESCRIPTION

Figure 1:
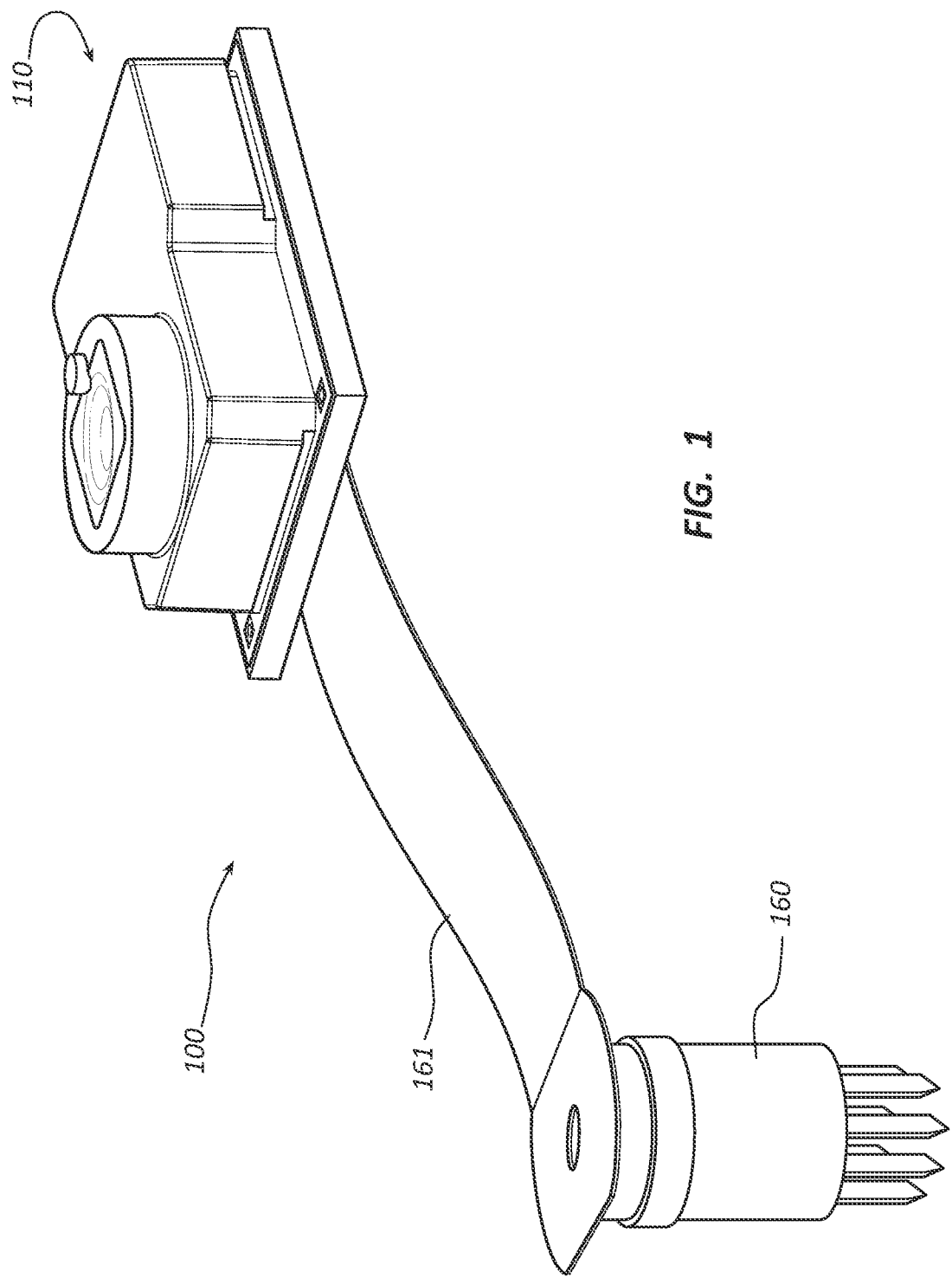
FIG. 1 is a perspective view of an embodiment of a sensor device assembly.

Extracorporeal perfusion of a patient's blood may be used to sustain a patient's life when the patient is experiencing heart transplant, open heart surgery, heart failure, lung failure, etc. Extracorporeal perfusion may entail pumping a patient's blood through tubing using an external pump to temporarily replace a patient's heart, oxygenating and heating the blood, and returning the blood to the patient. In some instances, it may be desired to measure certain physiologic parameters of the blood during the extracorporeal perfusion. These physiologic parameters may include blood pressure, blood temperature, oxygen saturation, blood carbon dioxide level, blood pH, blood electrolytes air bubbles, etc. In certain instances, a sensor device assembly may be coupled to the tubing and in contact with the blood flowing through the tubing to sense and measure the physiologic parameters.

A sensor device assembly may be configured to measure blood pressure and blood temperature at a common site with a blood pressure sensor and a temperature sensor coupled to a common printed circuit board (PCB). In some embodiments, the sensor device assembly may comprise a housing defining a gel well, the PCB, a first sensor (e.g., temperature sensor) electrically coupled to the PCB, a second sensor (e.g., pressure sensor) electrically coupled to the PCB, and a connector electrically coupled to the PCB. The temperature sensor may be clad with a hemocompatible material and positioned within the gel well such that temperature sensor is in direct contact with the blood. In various embodiments, temperature sensor may be flush with the gel well or protrude into a flow of the blood within the tubing. The pressure sensor may be disposed at a base of the gel well. The gel well may be filled with a gel that surrounds the pressure sensor and transmits or propagates a pressure force from the blood to the pressure sensor such that the pressure sensor measures the blood pressure through interaction with the gel.

In another embodiment, the temperature sensor and the pressure sensor may be disposed at the bottom of the gel well and surrounded by gel such that neither sensor is in direct contact with the blood. In this embodiment, the gel is configured to transmit the pressure force to the pressure sensor and to be thermally conductive such that the temperature sensor measures the blood temperature through interaction with the gel.

A method of measuring at least two physiologic parameters of blood at a substantially common site in an extracorporeal circuit may include the steps of obtaining the sensor device assembly and coupling the sensor device assembly to the extracorporeal circuit such that at least one of the sensors of the sensor device assembly is in direct contact with the blood flowing through the circuit.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

FIGS. 1-9 illustrate different views of sensor device assemblies and related components. In certain views each assembly may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIGS. 1-6 depict one embodiment of a sensor device assembly 100. In the illustrated embodiment, the sensor device assembly 100 is partially comprised of a sensor device 110 and a connector 160. As shown in FIG. 1, the connector 160 is electrically coupled to the sensor device 110 via a ribbon cable 161. In other embodiments, the connector 160 may be electrically coupled to the sensor device 110 via any other suitable cable or connection system. The connector 160 may be a pin type connector as depicted in FIG. 1. In other embodiments, the connector 160 may be any other suitable connector 160, such as a contact connector. In still other embodiments, the sensor device assembly 100 may not include a connector 160. Instead, signals from the sensor device 110 may be transmitted wireless to a receiver.

Figure 2:
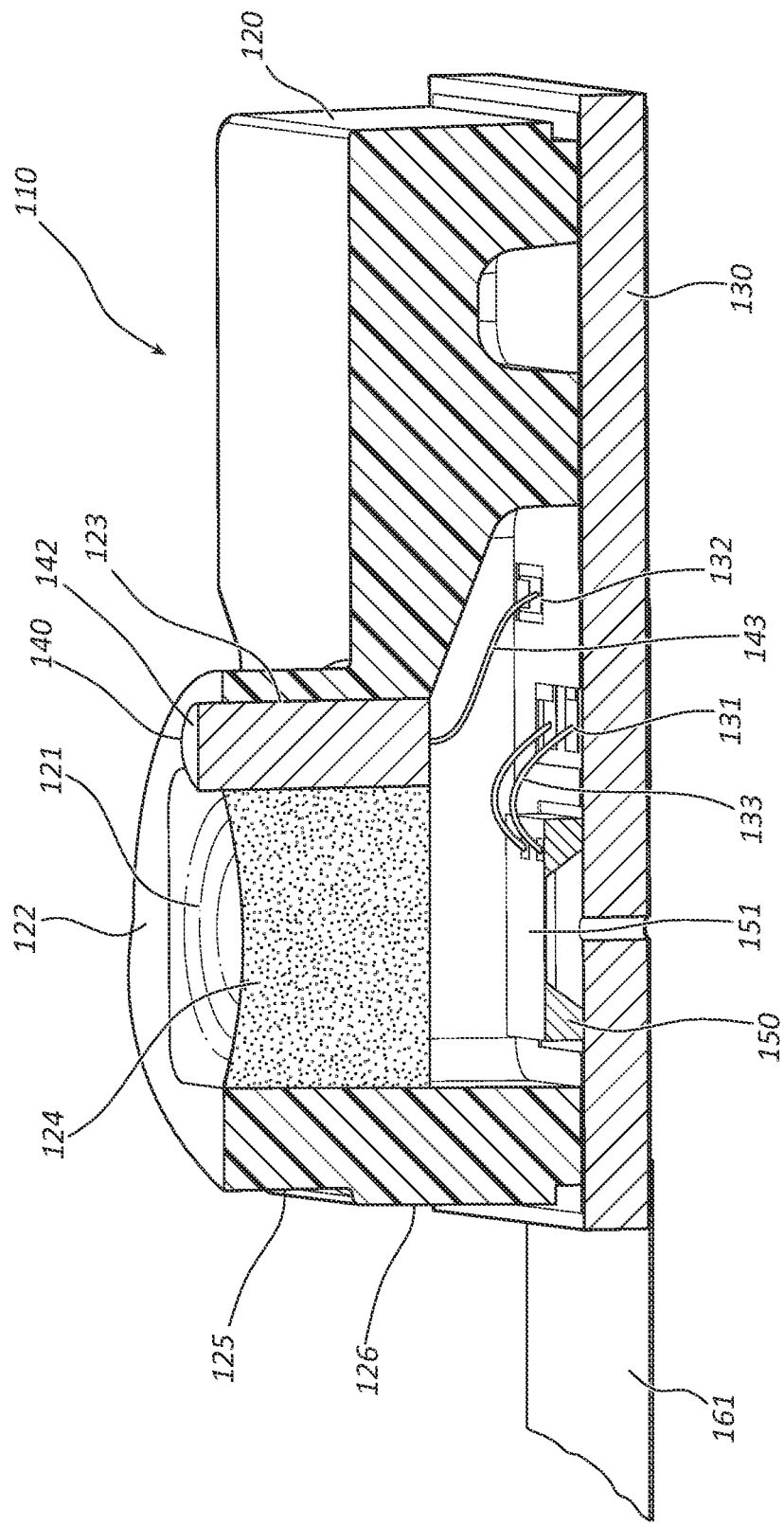
FIG. 2 is a cross-sectional perspective view of a sensor device of the sensor device assembly of FIG. 1.

As illustrated in FIG. 2, the sensor device 110 may include a housing 120, a PCB member 130, a first sensor (in the illustrated embodiment, the first sensor is a temperature sensor 140), a second sensor (in the illustrated embodiment, the second sensor is a pressure sensor 150), and a gel 124. The housing 120 may be coupled to the PCB member 130 to form a fluid tight seal between a lower surface of the housing 120 and an upper surface of the PCB member 130. The housing 120 may be coupled to the PCB member 130 using any suitable technique. For example, the housing 120 can be coupled to the PCB member 130 by bonding, adhering, welding, etc.

Figure 3:
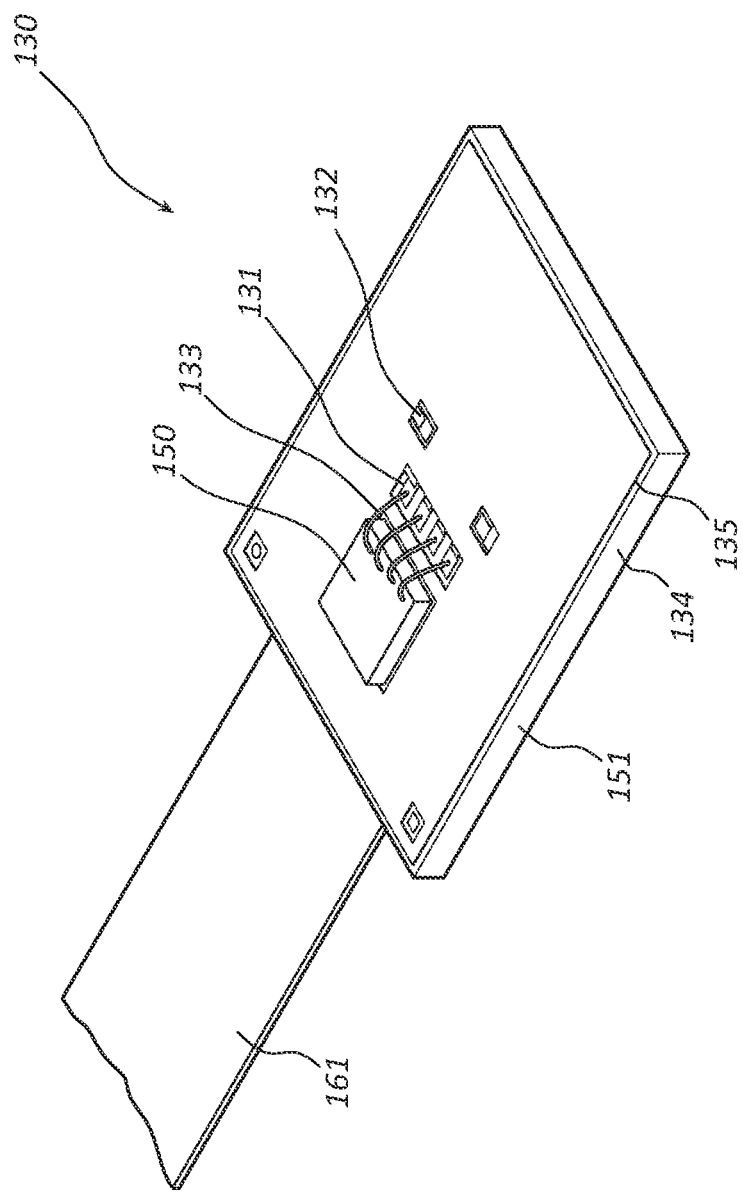
FIG. 3 is a perspective view of a printed circuit board of the sensor device of FIG. 2.

Referring to FIGS. 2 and 3, the PCB member 130 may be a ceramic PCB comprising a ceramic or glass-reinforced epoxy laminate substrate 134 and a copper conductive layer 135. In the illustrated embodiment, the PCB member 130 includes a pressure sensor pad 131 and a temperature sensor pad 132. In some embodiments, the PCB member 130 may include additional pads for other types of sensors. The pressure sensor 150 is coupled to the PCB member 130 with wires 133 electrically coupling the pressure sensor 150 to the pressure sensor pad 131. The pressure sensor may be any suitable type of pressure sensor. The ribbon cable 161 is electrically coupled to the PCB member 130.

FIGS. 2, 4A, and 4B illustrate the housing 120. As illustrated, the housing 120 defines a gel well 121 disposed adjacent a first end 126 of the housing 120. The housing 120 may be formed from any suitable material. For example, the housing 120 may be formed from polycarbonate, nylon, polyetheretherketone, polyaryle ether ketone, polyetherketoneketone, polytetrafluoroethylene, polysulfone, polyphenylsulfone, etc. The gel well 121 may be configured to allow measurement of both blood pressure and temperature at a substantially common site. In the illustrated embodiment, the gel well 121 includes a rim 122 circumferentially surrounding the gel well 121. A sensor slot 123 may be disposed in a wall 125 of the gel well 121 and extend downward from the rim 122. As depicted, the sensor slot 123 is disposed in the wall 125 away from the first end 126 of the housing 120. In other embodiments, the sensor slot 123 may be disposed in the wall 125 adjacent the first end 126 of the housing 120. The sensor slot 123 may be configured for coupling the temperature sensor 140 to the housing 120 via an interference fit. In some embodiments, the temperature sensor 140 can be coupled to the housing 120 using any other suitable technique, such as gluing, bonding, insert molding, etc.

Figure 5B:
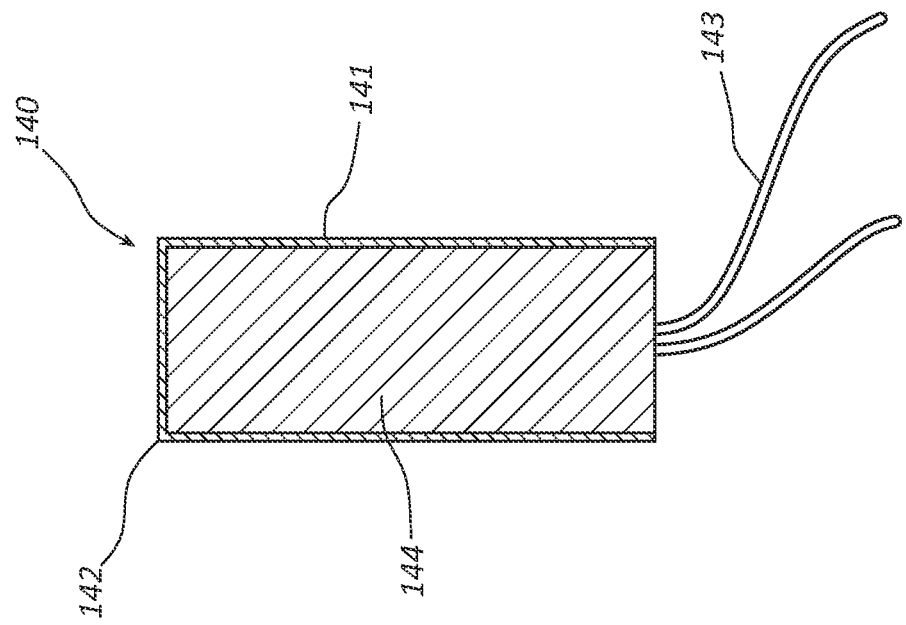
FIG. 5B is a longitudinal cross-sectional view of the temperature sensor of FIG. 5A.
Figure 5A:
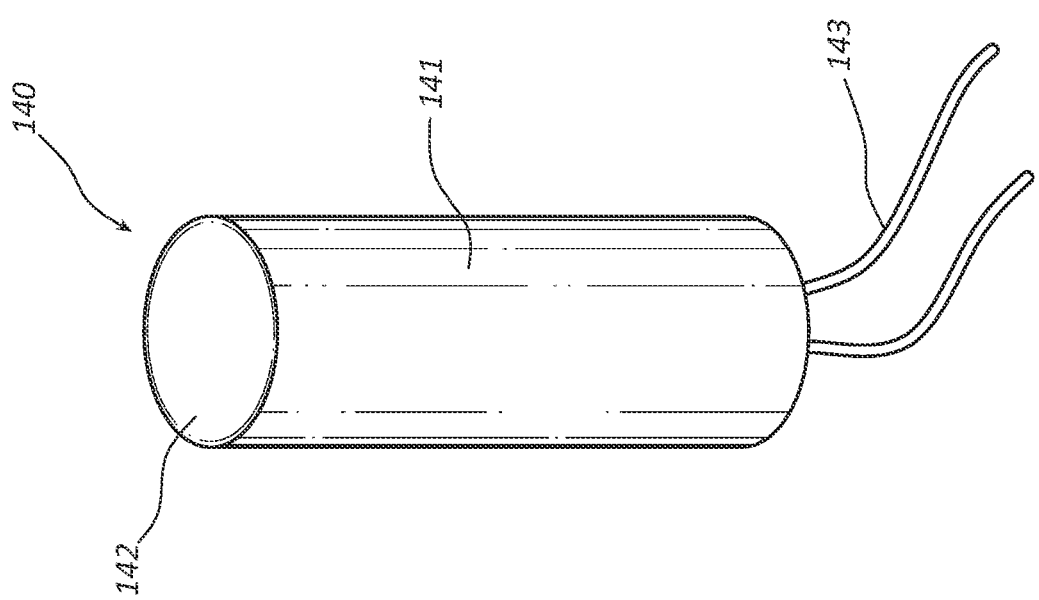
FIG. 5A is a perspective view of the temperature sensor of the sensor device of FIG. 2.

As shown in FIGS. 2, 5A, and 5B, the temperature sensor 140 may be disposed within the sensor slot 123 of the gel well 121. In another embodiment, the temperature sensor 140 may be disposed within a central portion of the gel well 121. Other relative positions of the temperature sensor 140 are likewise within the scope of this disclosure. The temperature sensor 140 may be any suitable type of temperature sensor 140, such as a resistance temperature detector, a negative temperature coefficient thermistor, a positive temperature coefficient thermistor, a thermocouple, etc. The temperature sensor 140 includes wires 143 configured to electrically couple the temperature sensor 140 to the temperature sensor pad 132 of the PCB member 130. The temperature sensor 140 can be configured to have an accuracy of about plus or minus 0.1 degree Celsius and a reaction time of about 10 to 15 seconds. The temperature sensor 140 may be cylindrical in shape and have a diameter of about 0.8 mm. In other embodiments, the temperature sensor 140 may be of any other suitable shape and size.

The temperature sensor 140 may include a cladding 141 surrounding a sensor member 144. The cladding 141 may include any suitable hemocompatible material. For example, the cladding 141 may include polyimide, stainless steel, copper, carbon, aluminosilicate, ceramic, glass glaze, parylene, polytetrafluoroethylene, etc. In the depicted embodiment, the cladding 141 is a polyimide dead-end tube (e.g., tube that is closed at one end) into which the sensor member 144 is disposed. In other embodiments, the cladding 141 may be applied to the sensor member 144 using any suitable technique, such as dip coating, sputter coating, vapor deposition, etc. A thickness of the cladding 141 may range from about 0.025 mm to about 0.254 mm. The cladding 141 may be configured to electrically isolate the sensor member 144 from the blood and to provide a hemocompatible blood contact surface while minimizing attenuation of the measured blood temperature. In some embodiments wherein the cladding 141 is configured to electrically isolate the sensor member 144, the cladding may be configured to isolate the sensor 144 to comply with a 5 kV isolation test.

As illustrated in FIG. 2, the temperature sensor 140 may be disposed relative to the rim 122 of the gel well 121 such that a first end 142 of the temperature sensor 140 may directly contact the blood. In this configuration, the temperature sensor 140 may measure a blood temperature directly with a minimal gradient or attenuation. As depicted, the first end 142 can protrude above the rim 122. A height of the protrusion may range from about 0.001 inch to about 0.100 inch, from about 0.025 inch to about 0.075 inch, and may be about 0.050 inch. Alternatively, the first end 142 may be flush with the rim 122 such that the first end 142 neither protrudes above the rim 122 nor is recessed below the rim 122. The height of the first end 142 with respect to the rim 122 may be configured such that, blood may flow over the temperature sensor 140 while minimizing turbulence, minimizing damage to the blood, and/or minimizing creation of thrombosis downstream from the temperature sensor 140.

As shown in FIG. 2, the gel well 121 may be substantially filled with a gel 124. The gel 124 may be a silicone material or any other suitable material. The gel 124 may surround the pressure sensor 150. The gel 124 may be configured to electrically isolate the pressure sensor 150 and to transmit a pressure force from the blood adjacent a top surface of the gel 124, through the gel 124, and to the diaphragm 151 of the pressure sensor 150. The gel 124 may form a meniscus within the gel well 121 such that the top surface of the gel 124 is below the rim 122. In other embodiments, the upper surface of the gel 124 may be flush with the rim 122 or domed above the rim 122. The gel 124 may at least partially surround and isolate the temperature sensor 140. In some embodiments, the gel 124 may produce a fillet around the temperature sensor 140 that protrudes above the top of the gel well 121.

The sensor device assembly 100 may be configured to measure both blood pressure and blood temperature at a substantially common location. An exemplary application of the sensor device assembly 100 is the sensor device assembly 100 may be coupled to a perfusion circuit for extracorporeal circulation of blood to support a patient during cardiovascular procedures or failure. Another exemplary application is coupling to an extracorporeal hemodialysis circuit for treatment of a kidney failure patient. In some embodiments, the sensor device assembly 100 may include sensors configured to measure or sense blood oxygen saturation, blood carbon dioxide level, blood pH, blood electrolytes, air bubbles in the blood, etc.

Figure 6:
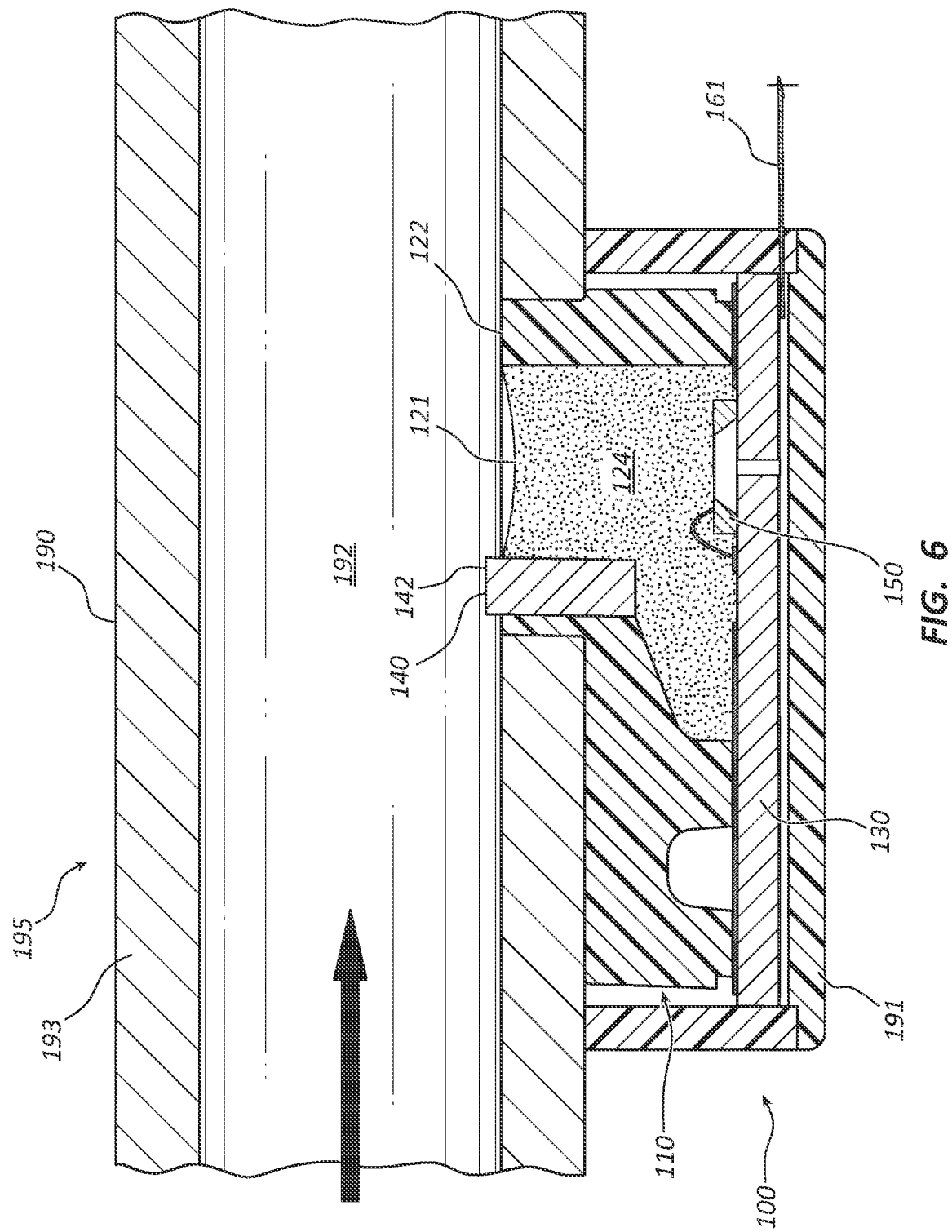
FIG. 6 is a cross-sectional view of the sensor device of FIG. 2 coupled to a blood flow tubing.

FIG. 6 illustrates the sensor device assembly 100 coupled to tubing 190 of an extracorporeal circuit 195. The sensor device 110 may be disposed within an outer housing 191 adjacent a wall 193 of the tubing 190. The gel well 121 may extend through the wall 193 such that the rim 122 is flush with an inner surface of the wall 193. In this configuration, the gel 124 is exposed to the blood flowing through a lumen 192 of the tubing 190 without the gel well 121 disturbing the flow of blood and causing thrombus formation. The gel 124 can transmit a pressure force exerted on the top surface of the gel 124 by the blood to the pressure sensor 150 to measure a blood pressure within the tubing 190. When the pressure force is sensed by the pressure sensor 150, the pressure sensor 150 can generate an electrical signal that is transmitted via the circuitry of the PCB member 130, through the ribbon cable 161, and connector 160 (not shown) to a display and/or controller (not shown). The blood pressure within the tubing 190 may be either manually or automatically controlled by adjustments made to a fluid pump operably coupled to the extracorporeal circuit 195 based on the measured blood pressure.

The temperature sensor 140 is depicted disposed partially within the gel well 121. The first end 142 of the temperature sensor 140 is shown protruding above the rim 122 of the gel well 121 and into the lumen 192 of the tubing 191. In other embodiments, the first end 142 may be positioned flush with or below the rim 122 to minimize disturbance of the blood flow, bubble creation, and thrombosis. In either embodiment, the first end 142 is configured to be in direct contact with the blood flowing through the tubing 191 such that the temperature sensor 140 directly senses the temperature of the blood. Upon sensing the blood temperature, the temperature sensor 140 can generate an electrical signal that is transmitted via the circuitry of the PCB member 130, ribbon cable 161, and connector 160 (not shown) to a display and/or controller. The blood temperature within the tubing 190 may be either manually or automatically controlled by adjustments made to a heater based on the measured blood temperature.

In the depicted embodiment of FIG. 6, the temperature sensor 140 is disposed on an upstream side of the gel well 121. In other words, the blood flowing within the tubing 190 in the direction indicated by the arrow, contacts the temperature sensor 140 before contacting the gel 124. During some applications with this configuration, the temperature sensor 140 may induce turbulence in the blood flow and affect the blood pressure force on the gel 124 which may influence the blood pressure measurement. Embodiments wherein the sensors or PCB are configured to compensate for such effects are within the scope of this disclosure. In some embodiments, the temperature sensor 140 may be disposed on the downstream side of the gel well 121. In other words, the blood flowing within the tubing 190 in the direction of the arrow, contacts the gel 124 before contacting the temperature sensor 140. In such configurations, possible flow turbulence created by the temperature sensor 140 may minimally affect the blood pressure force on the gel 124 and the blood pressure measurement, as such turbulence is not induced over the gel 124.

Figure 7:
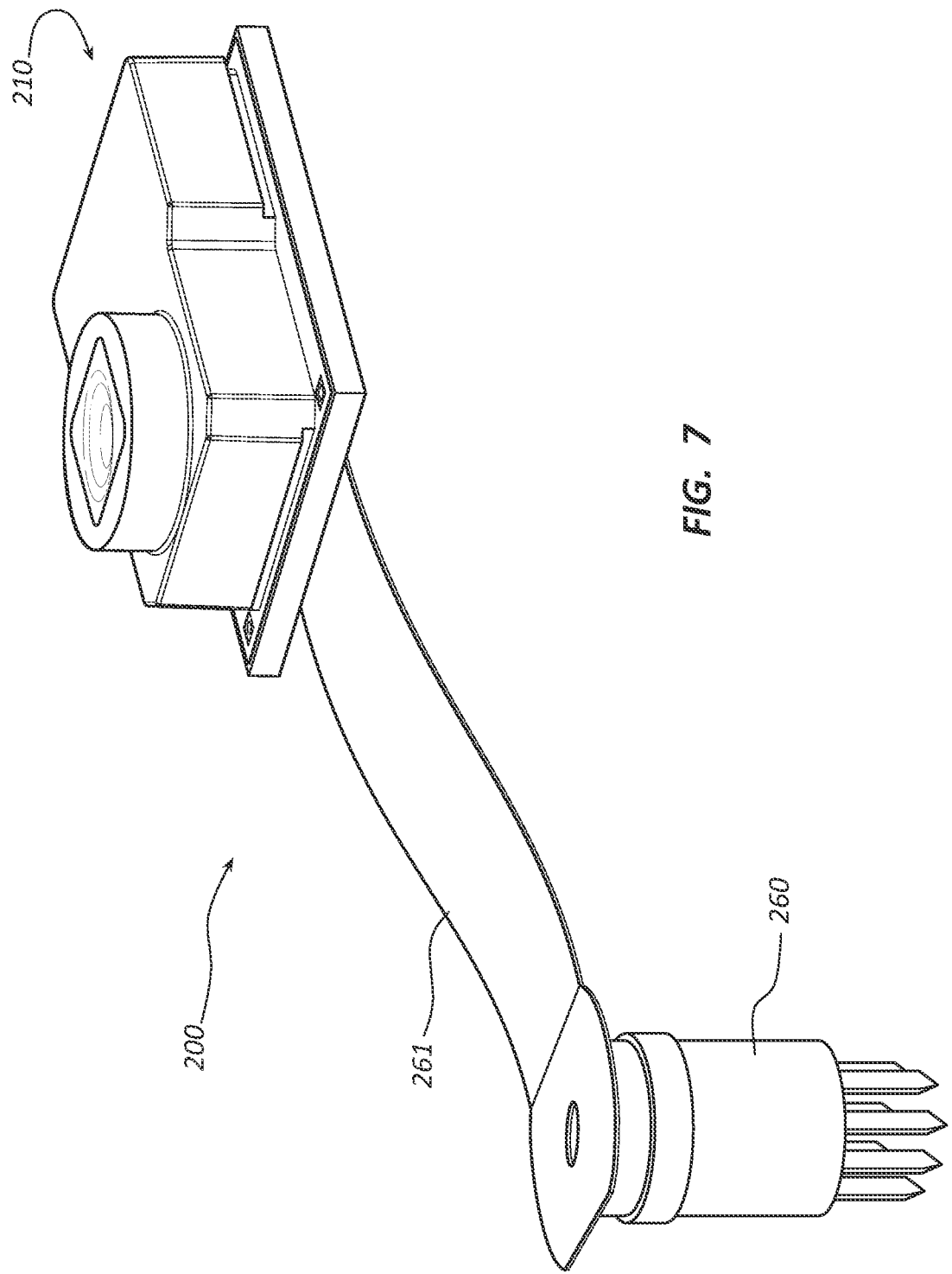
FIG. 7 is a perspective view of another sensor device assembly.
Figure 8:
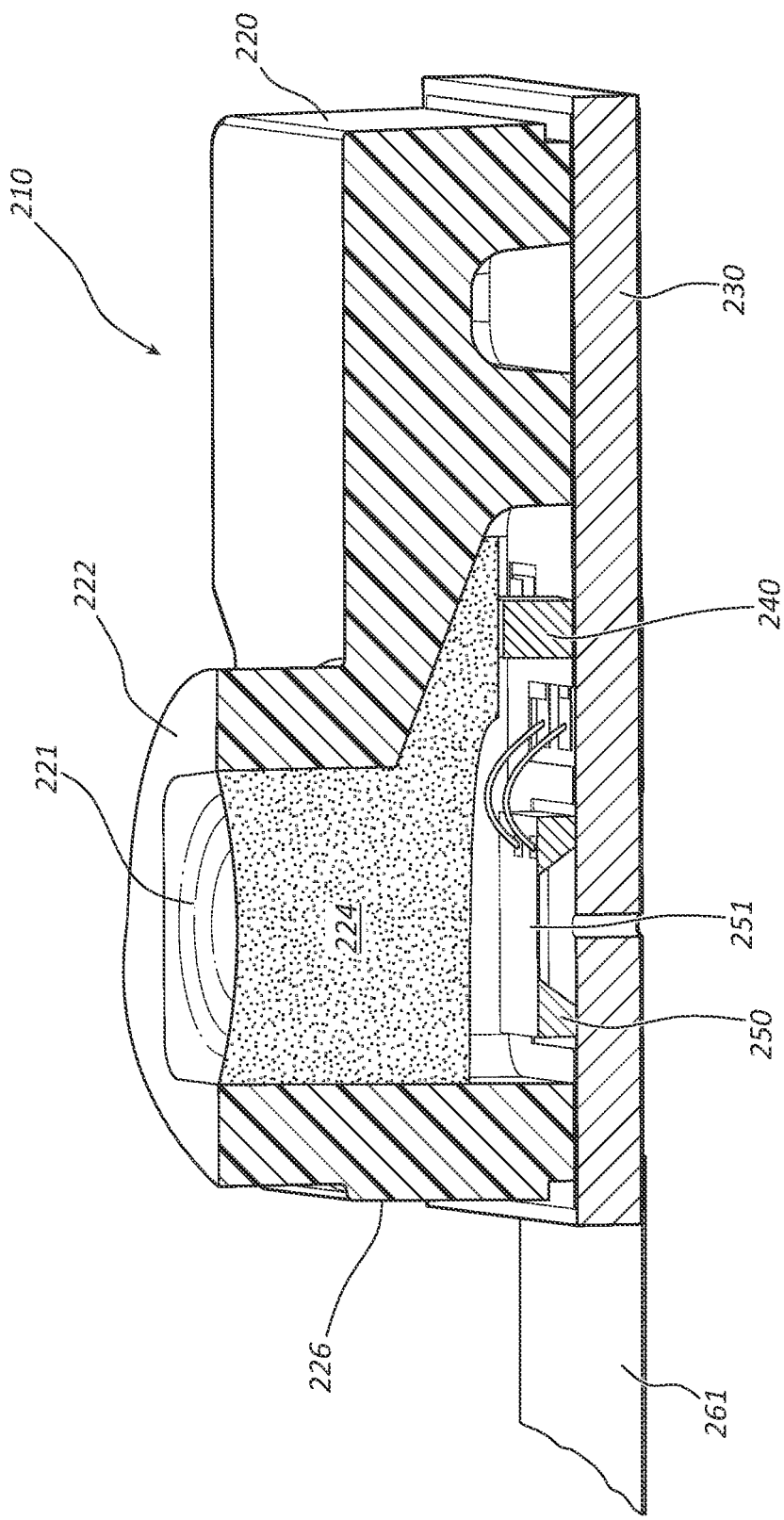
FIG. 8 is a cross-sectional perspective view of a sensor device of the sensor device assembly of FIG. 7.
Figure 9:
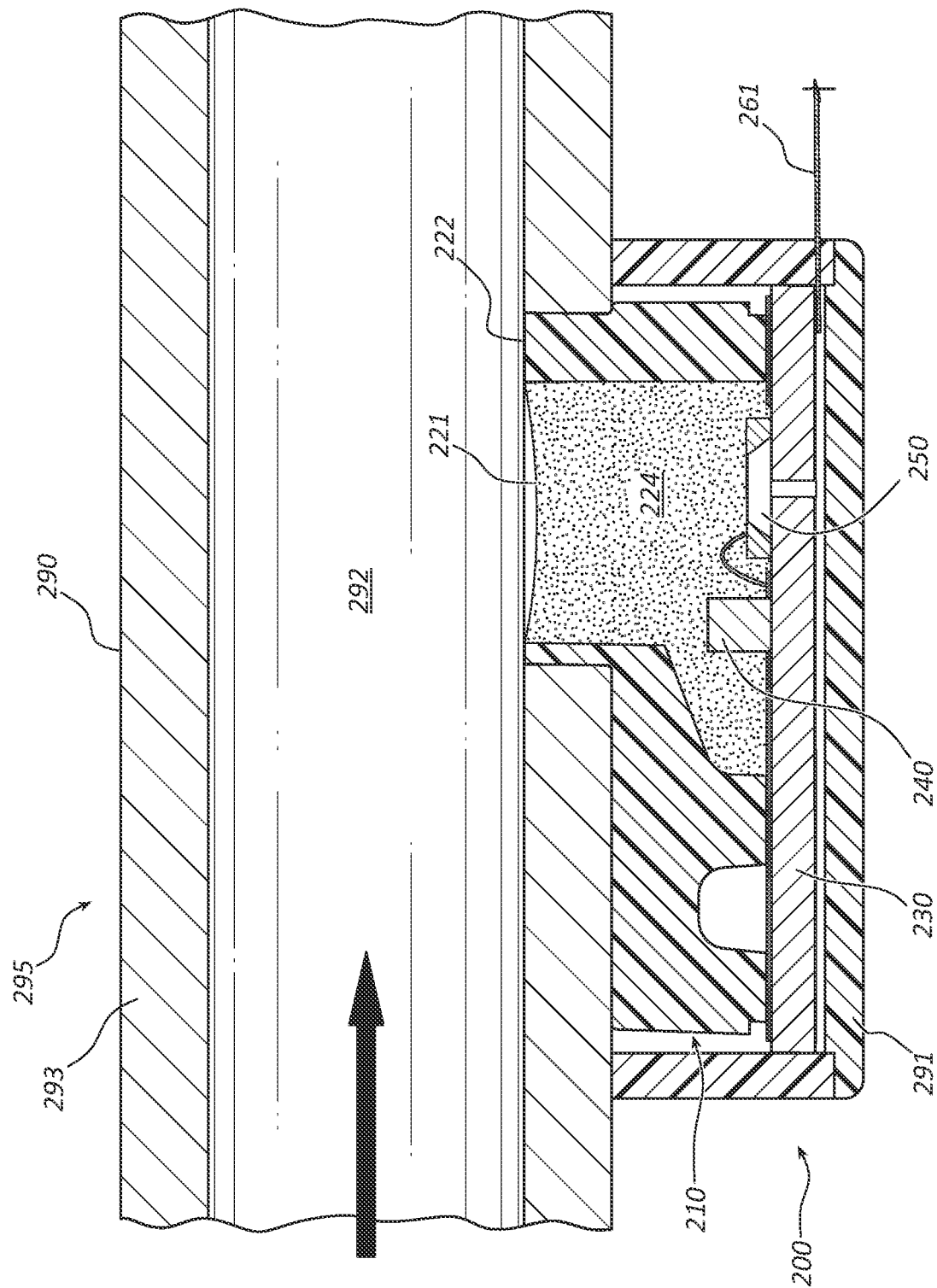
FIG. 9. is a cross-sectional view of the sensor device of FIG. 8 coupled to a blood flow tubing.

FIGS. 7-9 depict an embodiment of a sensor device assembly 200 that resembles the sensor device assembly 100 described above in certain respects. Accordingly, like features are designated with like reference numerals, with the leading digit incremented to "2." For example, the embodiment depicted in FIGS. 7-9 includes a sensor device 210 that may, in some respects, resemble the sensor device 110 of FIG. 1. Relevant disclosure set forth above regarding similarly identified features thus may not be repeated hereafter. Moreover, specific features of the sensor device assembly 100 and related components shown in FIGS. 1-6 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the sensor device assembly 200 and related components depicted in FIGS. 7-9. Any suitable combination of the features, and variations of the same, described with respect to the sensor device assembly 100 and related components illustrated in FIGS. 1-6 can be employed with the sensor device assembly 200 and related components of FIGS. 7-9, and vice versa.

FIGS. 7-9 illustrate another embodiment of a sensor device assembly 200. As shown in FIG. 7, the sensor device assembly 200 can include a sensor device 210 and a connector 260 coupled to the sensor device 210 via a ribbon cable 261.

As illustrated in FIG. 8, the sensor device 210 may include a housing 220, a PCB member 230, a first sensor 240 (e.g., temperature sensor), a second sensor 250 (e.g., pressure sensor), and a gel 224. The pressure sensor may be any suitable type of pressure sensor. In the illustrated embodiment, the ribbon cable 261 is electrically coupled to the PCB member 230.

As illustrated, the housing 220 defines a gel well 221 disposed adjacent a first end 226 of the housing 220. The gel well 221 includes a rim 222 circumferentially surrounding the gel well 221. The gel well 221 includes a portion extending away from the first end 226 of the housing 220. The temperature sensor 240 may be disposed within the portion of the gel well 221 extending away from the first end 226 of the housing 220. The temperature sensor 240 may be any suitable type of sensor, such as a resistance temperature detector, a negative temperature coefficient thermistor, a positive temperature coefficient thermistor, a thermocouple, etc.

As shown in FIG. 8, the gel well 221 may be substantially filled with a gel 224. The gel 224 may be a silicone material or any other. The gel 224 may surround the pressure sensor 250 and the temperature sensor 240. The gel 224 may be configured to electrically isolate the pressure sensor 250 and the temperature sensor 240. The gel 224 can be substantially non-compressible and configured to transmit a pressure force from the blood adjacent a top surface of the gel 224, through the gel 224, and to the diaphragm 251 of the pressure sensor 250. The gel 224 can be thermally conductive such that the temperature of the blood in contact with an upper surface of the gel may be transmitted through the gel 224 to the temperature sensor 240. The blood temperature may be attenuated between about one degree Celsius and 15 degrees Celsius as the blood temperature is transmitted through the gel 224 over a response time of up to 10 minutes or more. The gel 224 may form a meniscus within the gel well 221 such that a top surface of the gel 224 is below the rim 222. In other embodiments, the top surface of the gel 224 may be flush with the rim 222 or domed above the rim 222.

FIG. 9 illustrates the sensor device assembly 200 coupled to tubing 290 of an extra corporeal circuit 295. The sensor device 210 may be disposed within an outer housing 291 adjacent a wall 293 of the tubing 290. The gel well 221 may extend through the wall 293 such that the rim 222 is flush with an inner surface of the wall 293. The top surface of the gel 224 can be exposed to the blood flowing through a lumen 292 of the tubing 290 in a direction indicated by the arrow. The gel 224 can transmit a pressure force exerted on the upper surface of the gel 224 by the blood to the pressure sensor 250 to measure a blood pressure within the tubing 290.

The gel 224 can also transmit the blood temperature from substantially the same location as the pressure force through the gel 224 and to the temperature sensor 240. The blood temperature may be transmitted through the gel 224 by warming of the gel 224 by the blood. The temperature of the gel 224 at the temperature sensor 240 may be different than the blood temperature at the top surface of the gel 224 due to a loss of heat to surrounding structures, such as the housing 220 and the PCB member 230. In other embodiments, a heat conductor or heat pipe may be disposed in the gel 224. A top end of the heat conductor can be disposed at the top surface of the gel 224 and a bottom end of the heat conductor can be disposed adjacent the temperature sensor 240. The heat conductor may be configured to provide thermal heat transfer from the blood to the temperature sensor 240 while also providing electrical isolation. When the temperature sensor 240 senses a temperature of the gel 224 adjacent to the temperature sensor 240, an electrical signal (e.g., voltage) may be transmitted through circuitry of the PCB member 230, through the ribbon cable 261, through the connector 260 (not shown), and to a processor (not shown) where the processor may receive the signal and correct the attenuated sensed temperature using an algorithm. The corrected temperature may then be transmitted to a display and/or controller such that a heater may be adjusted manually or automatically to adjust the blood temperature.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A sensor device, comprising:
 a housing comprising a gel well;
 a printed circuit board member;
 a first sensor electrically coupled to the printed circuit board member; and
 a second sensor electrically coupled to the printed circuit board member,
 wherein the first sensor is configured to measure a first parameter of a physiologic fluid and the second sensor is configured to measure a second parameter of the physiologic fluid at a common site of a perfusion circuit,
 wherein the first sensor is at least partially disposed within the gel well of the housing, and
 wherein a first end of the first sensor protrudes above a rim of the gel well.

2. The sensor device of claim 1, wherein the first sensor is in direct contact with the physiologic fluid.

3. The sensor device of claim 1, wherein the first sensor is a temperature sensor, and wherein the first parameter is temperature.

4. The sensor device of claim 3, wherein the temperature sensor comprises a cladding.

5. The sensor device of claim 4, wherein the cladding comprises any one of polyimide, stainless steel, copper, carbon, aluminosilicate, ceramic, glass glaze, parylene, and polytetrafluoroethylene.

6. The sensor device of claim 5, wherein the cladding is any one of a dead-end tube and a dip coating.

7. The sensor device of claim 1, wherein the first end of the first sensor protrudes above the rim of the gel well a distance of between 0.001 inch and 0.100 inch.

8. The sensor device of claim 1, wherein the second sensor is a pressure sensor, and the second parameter is fluid pressure.

9. The sensor device of claim 1, wherein the second sensor is disposed at a base of the gel well of the housing, wherein the gel well is filled with a gel, and wherein the gel surrounds the second sensor.

10. The sensor device of claim 1, further comprising a third sensor to measure a third physiologic parameter.

11. A sensor assembly, comprising:
    a housing comprising a gel well;
    a printed circuit board member;
    a pressure sensor electrically coupled to the printed circuit board member;
    a temperature sensor electrically coupled to the printed circuit board member; and
    a connector electrically coupled to the printed circuit board;
    wherein the temperature sensor is configured to measure a blood temperature and the pressure sensor is configured to measure a blood pressure at a common site of a perfusion circuit, and
    wherein the temperature sensor is at least partially disposed within the gel well of the housing.

12. The sensor assembly of claim 11, wherein a first end of the temperature sensor is flush with a rim of the gel well.

13. The sensor assembly of claim 11, wherein a first end of the temperature sensor protrudes above a rim of the gel well.

14. A method of measuring physiologic parameters of a fluid, comprising: obtaining a sensor device comprising:
    a housing comprising a gel well;
    a first sensor;
    a second sensor,
    wherein the first sensor is at least partially disposed within the gel well of the housing, and
    wherein a first end of the first sensor protrudes above a rim of the gel well; and
    exposing the sensor device to the fluid;
    wherein the first sensor is in direct contact with the fluid.

15. The method of claim 14, wherein the first sensor is a temperature sensor.

16. The method of claim 14, further comprising measuring a temperature and pressure of the fluid at a common site.

* * * * *